United States Patent
Jung

(10) Patent No.: US 12,383,733 B2
(45) Date of Patent: *Aug. 12, 2025

(54) IONTOPHORESIS-BASED PATCH TYPE MEDICINE ABSORPTION DEVICE

(71) Applicant: ROOTONIX Co., Ltd., Seoul (KR)

(72) Inventor: Dae Kwon Jung, Seoul (KR)

(73) Assignee: ROOTONIX Co., Ltd., Seoul (KR)

( * ) Notice: Subject to any disclaimer, the term of this patent is extended or adjusted under 35 U.S.C. 154(b) by 321 days.

This patent is subject to a terminal disclaimer.

(21) Appl. No.: 18/070,430

(22) Filed: Nov. 28, 2022

(65) Prior Publication Data

US 2023/0092631 A1     Mar. 23, 2023

Related U.S. Application Data

(63) Continuation-in-part of application No. 17/232,123, filed on Apr. 15, 2021, now Pat. No. 11,534,598.

(30) Foreign Application Priority Data

Oct. 8, 2020   (KR) .................. 10-2020-0130081

(51) Int. Cl.
  *A61N 1/30*     (2006.01)
  *A61K 9/00*     (2006.01)
  (Continued)

(52) U.S. Cl.
  CPC ............ *A61N 1/306* (2013.01); *A61K 9/0009* (2013.01); *A61K 9/7023* (2013.01); *A61N 1/0492* (2013.01)

(58) Field of Classification Search
  None
  See application file for complete search history.

(56) References Cited

U.S. PATENT DOCUMENTS

| | | | |
|---|---|---|---|
| 6,687,536 B1* | 2/2004 | Beck | A61N 1/325 604/289 |
| 2004/0260212 A1* | 12/2004 | Cho | A61N 1/30 601/72 |

(Continued)

FOREIGN PATENT DOCUMENTS

| | | |
|---|---|---|
| JP | 2001-520527 A | 10/2001 |
| JP | 3158303 U | 3/2010 |

(Continued)

*Primary Examiner* — Mallika D Fairchild
(74) *Attorney, Agent, or Firm* — Park, Kim & Suh, LLC

(57) ABSTRACT

Disclosed is an iontophoresis-based patch type medicine absorption device for allowing a medicine for medical treatment or a functional substance for skin care to be effectively absorbed into a user's skin by causing iontophoresis on the user's skin through a conductive patch. The iontophoresis-based patch type medicine absorption device for allowing the medicine for medical treatment or the functional substance for the skin care to be absorbed into the user's skin by the iontophoresis includes a medicine absorption device body that generates power to cause the iontophoresis. The medicine absorption device body includes a power circuit that is provided in an interior space of a body and that includes a power unit that generates the power for the iontophoresis and one or more electrodes to which the power is applied, and a bridge that is provided so as to be combinable with the body and that receives the power through the one or more electrodes. The bridge includes a bridge body provided so as to be combinable with the body and a plurality of bridge legs arranged along a circumferential direction of the bridge body and formed of a conductive material.

20 Claims, 13 Drawing Sheets

(51) Int. Cl.
 A61K 9/70 (2006.01)
 A61N 1/04 (2006.01)

(56) References Cited

U.S. PATENT DOCUMENTS

| | | | |
|---|---|---|---|
| 2010/0137779 | A1 | 6/2010 | Seitz |
| 2013/0023815 | A1 | 1/2013 | Imran et al. |
| 2014/0135679 | A1 | 5/2014 | Mann et al. |
| 2015/0182473 | A1* | 7/2015 | Bosnyak .............. A61K 9/0092 |
| | | | 604/20 |
| 2017/0095660 | A1* | 4/2017 | Yoo .......................... A61N 1/30 |
| 2017/0189227 | A1* | 7/2017 | Brunson ................. A61N 1/325 |

FOREIGN PATENT DOCUMENTS

| | | |
|---|---|---|
| JP | 2011-092543 A | 5/2011 |
| KR | 10-2014-0042786 A | 4/2014 |
| KR | 10-1526462 B1 | 6/2015 |
| KR | 10-1533718 B1 | 7/2015 |
| KR | 10-1916816 B1 | 11/2018 |
| KR | 10-2098969 B1 | 4/2020 |
| KR | 10-2123082 B1 | 6/2020 |

* cited by examiner

IONTOPHORESIS-BASED PATCH TYPE MEDICINE ABSORPTION DEVICE

CROSS-REFERENCE TO RELATED APPLICATIONS

This application is a continuation-in-part of U.S. patent application Ser. No. 17/232,123, filed on Apr. 15, 2021, currently pending, which claims the benefit of Korean Patent Application No. 10-2020-0130081, filed on Oct. 8, 2020, which is hereby incorporated by reference as if fully set forth herein.

BACKGROUND

Embodiments of the inventive concept described herein relate to an iontophoresis-based patch type medicine absorption device, and more particularly, relate to an iontophoresis-based patch type medicine absorption device for allowing a medicine for medical treatment or a functional substance for skin care to be effectively absorbed into a user's skin by causing iontophoresis on the user's skin through a conductive patch.

Recently, various methods for skin care, prevention of hair loss, or facilitation of hair growth have been proposed. Among the various methods, oral administration where a substance for skin care, prevention of hair loss, or facilitation of hair growth is taken through the mouth may be less effective and may cause several side effects because the substance does not directly act on the skin or scalp. As an alternative to the oral administration, a method for applying a functional substance to the skin or applying a substance for prevention of hair loss or facilitation of hair growth to the scalp has been proposed. However, this method has a limitation in that the substance is not effectively absorbed into the skin or scalp through hair follicles.

Iontophoresis has been introduced as a method for allowing a substance to be absorbed into the skin. The iontophoresis is a method for introducing various substances supplied to the skin into the stratum corneum by applying voltage. For example, when negative voltage is applied to a part to which a substance having negative charges is applied, the substance is moved into the stratum corneum by an electrostatic repulsive force.

However, the iontophoresis may cause an inconvenience to a user because the user has to consistently apply voltage to the skin using a voltage application device while introducing a functional substance for skin care into the stratum corneum. Furthermore, an introduction effect of the functional substance may be concentrated on an area of the skin to which voltage is applied by an electrode, and current may not be transferred to a peripheral portion of the skin that the electrode does not touch. Therefore, introduction performance of the functional substance may be degraded, and effects of the iontophoresis may not be maximized.

SUMMARY

Embodiments of the inventive concept provide an iontophoresis-based patch type medicine absorption device for allowing a medicine for medical treatment or a functional substance for skin care to be effectively absorbed into a user's skin by causing iontophoresis on the user's skin through a conductive patch.

Furthermore, embodiments of the inventive concept provide an iontophoresis-based patch type medicine absorption device for maintaining a state of being stably coupled to a conductive patch and radially expanding an iontophoresis generation area caused by micro-current.

Moreover, embodiments of the inventive concept provide an iontophoresis-based patch type medicine absorption device for transferring power (voltage or micro-current) for iontophoresis in a state of being coupled to a conductive patch attached to a user's skin.

In addition, embodiments of the inventive concept provide an iontophoresis-based patch type medicine absorption device for generating uniform iontophoresis on a user's skin to which a conductive patch is attached, by controlling distribution of micro-current transferred through the conductive patch.

According to an exemplary embodiment, an iontophoresis-based patch type medicine absorption device for allowing a medicine for medical treatment or a functional substance for skin care to be absorbed into a user's skin by iontophoresis includes a medicine absorption device body that generates power to cause the iontophoresis.

The medicine absorption device body includes a body having an interior space, a power circuit that is provided in the interior space and that includes a power unit (power supply) that generates the power for the iontophoresis and one or more electrodes to which the power is applied, and a bridge that is provided so as to be combinable with the body and that receives the power through the one or more electrodes.

The bridge includes a bridge body provided so as to be combinable with the body and a plurality of bridge legs arranged along a circumferential direction of the bridge body and formed of a conductive material. The plurality of bridge legs may receive the power through the one or more electrodes. The bridge body may be implemented with an insulator to electrically isolate the plurality of bridge legs.

The iontophoresis-based patch type medicine absorption device may further include a conductive patch that contains the medicine for medical treatment or the functional substance for the skin care and has conductivity and that is provided so as to be detachable from the user's skin. The conductive patch may be supported between the body and the plurality of bridge legs. The iontophoresis-based patch type medicine absorption device may transfer the power to the conductive patch through the plurality of bridge legs to allow micro-current to flow through the conductive patch and may generate a potential difference in the user's skin by the micro-current, which flows through the conductive patch, to cause the iontophoresis.

An upper part of each of the bridge legs may be formed of a conductive material, and a lower part of each of the bridge legs may be formed of an insulator, so that the medicine for medical treatment or the functional substance for the skin care of the conductive patch is effectively absorbed into the user's skin by causing the iontophoresis effectively on the user's skin through the conductive patch.

The bridge may further include a detachable part including a plurality of detachable protrusions protruding along an outer circumferential surface of the bridge body and a plurality of patch support parts provided on the plurality of bridge legs to support the conductive patch.

The plurality of bridge legs may be arranged to extend in a radial direction, with the bridge body as the center. The patch support parts may include a plurality of stoppers that protrude from outside ends of the plurality of bridge legs and that are formed to face outward in the radial direction. The conductive patch may include a plurality of cut-away portions formed in positions corresponding to the plurality of stoppers. The bridge may be coupled to the conductive patch by inserting the plurality of stoppers into the plurality of cut-away portions.

The body may have, in the center of one surface thereof, an opening for attachment and detachment of the bridge, and the body may have a plurality of insertion holes formed in positions corresponding to the plurality of detachable protrusions and formed along the circumferential direction from a periphery of the opening.

The bridge body may be provided to be inserted into the opening, and the plurality of detachable protrusions may be inserted through the plurality of insertion holes. The bridge may be coupled to the body by rotating the detachable protrusions inserted through the insertion holes.

A plurality of coupling holes for a coupling of the plurality of bridge legs and the bridge body may be formed in the bridge body along the circumferential direction. The plurality of bridge legs may include a plurality of coupling protrusions formed at inside ends of the bridge legs and coupled to the coupling holes. The coupling protrusions may be brought into contact with the electrodes in a state in which the bridge is coupled to the body.

Power of a first polarity may be applied to one or more electrodes among a plurality of electrodes of the power circuit, and power of a second polarity opposite to the first polarity may be applied to the remaining electrodes. The power of the first polarity may be applied to some of the plurality of bridge legs in a state in which the coupling protrusions are brought into contact with the electrodes, and the power of the second polarity may be applied to the other bridge legs.

The power circuit may further include a switching unit (switch) that sequentially switches polarities of power applied to the plurality of bridge legs.

The iontophoresis-based patch type medicine absorption device may further include a light source unit that is installed on a central portion of one surface of the body and that outputs light for skin care to the user's skin. The conductive patch may have an opening into which the bridge body is inserted. The light may reach the user's skin through the opening of the body, a central portion of the bridge body, and the opening of the conductive patch.

The medicine absorption device body may further include a charging part provided on one side of the body. The iontophoresis-based patch type medicine absorption device may further include a charging case that charges the medicine absorption device body. The charging case may include a receiving recess that receives the medicine absorption device body and a charger that charges, through the charging part, the medicine absorption device body received in the receiving recess. The conductive patch may include a plurality of sub-patches provided in a patch body, wherein the plurality of sub-patches are insulated from each other. Each of the plurality of sub-patches may be configured to receive the power for the iontophoresis from each of the one or more electrodes and each of the plurality of bridge legs.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
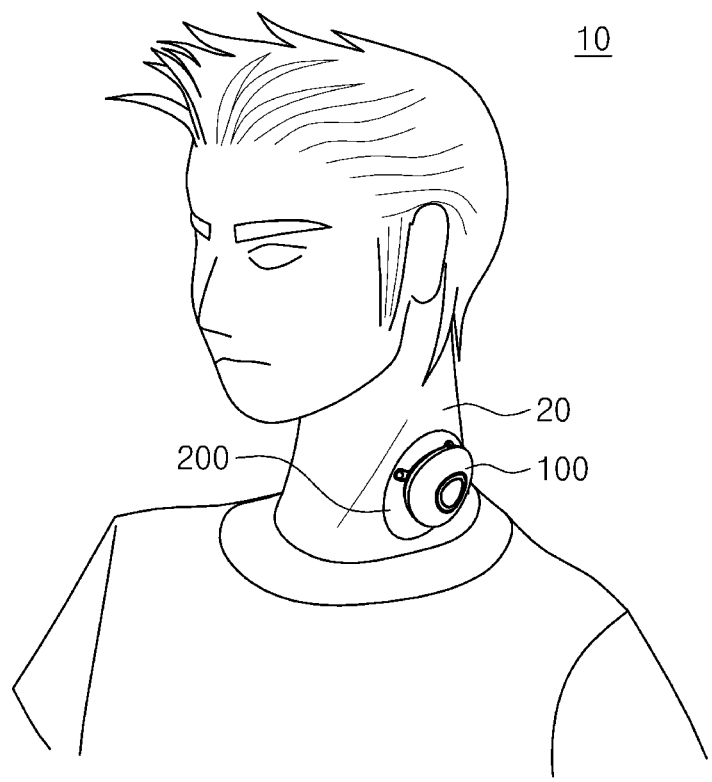
FIG. 1 is a view illustrating a usage state of an iontophoresis-based patch type medicine absorption device according to an embodiment of the inventive concept.

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide thorough understanding of the inventive concept to those skilled in the art to which the inventive concept pertains. Through the specification, identical reference numerals denote identical components. In this specification, when a portion "includes" a component, it may mean that the portion does not exclude another component unless specifically described to the contrary, but may further include another component.

Figure 2:
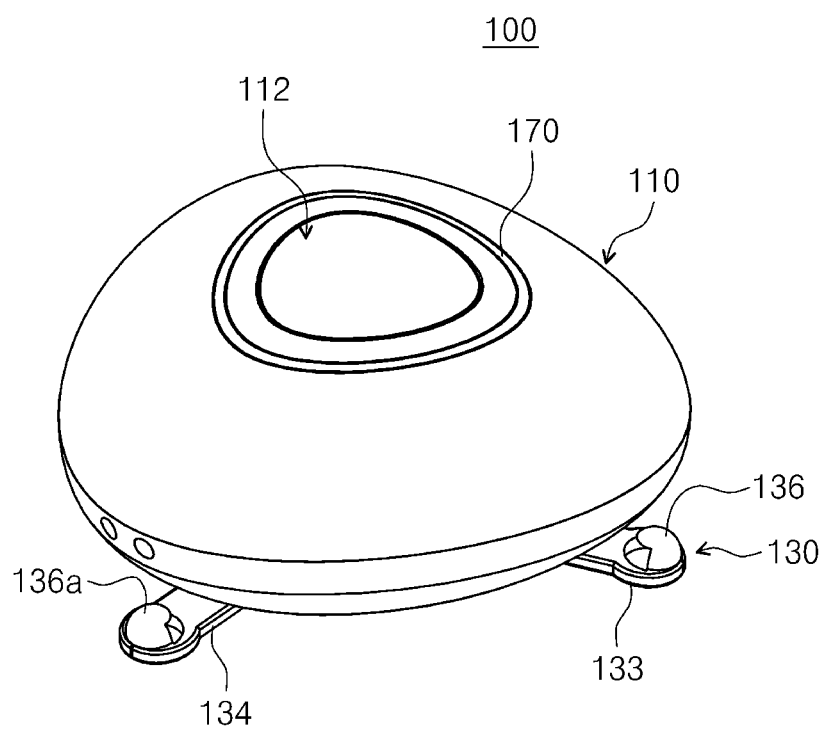
FIG. 2 is a perspective view of the iontophoresis-based patch type medicine absorption device according to the embodiment of the inventive concept.
Figure 3:
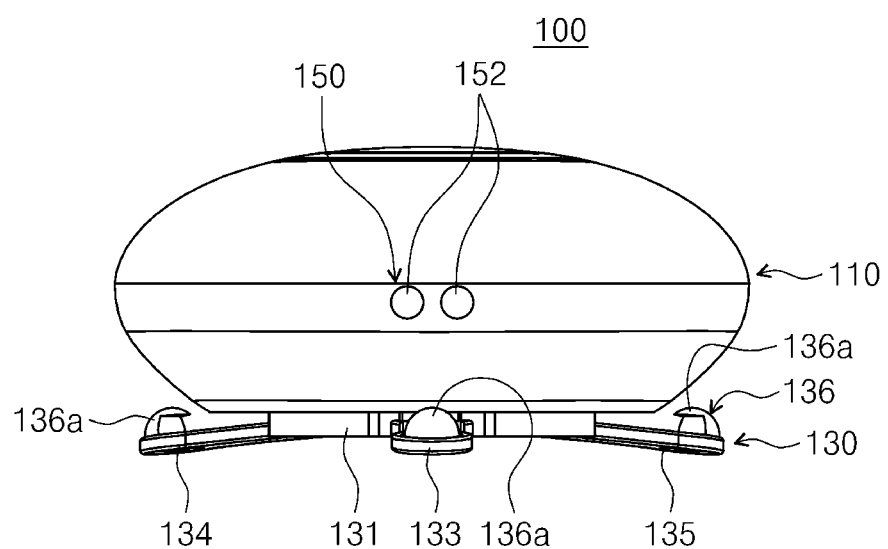
FIG. 3 is a side view of the iontophoresis-based patch type medicine absorption device according to the embodiment of the inventive concept.
Figure 4:
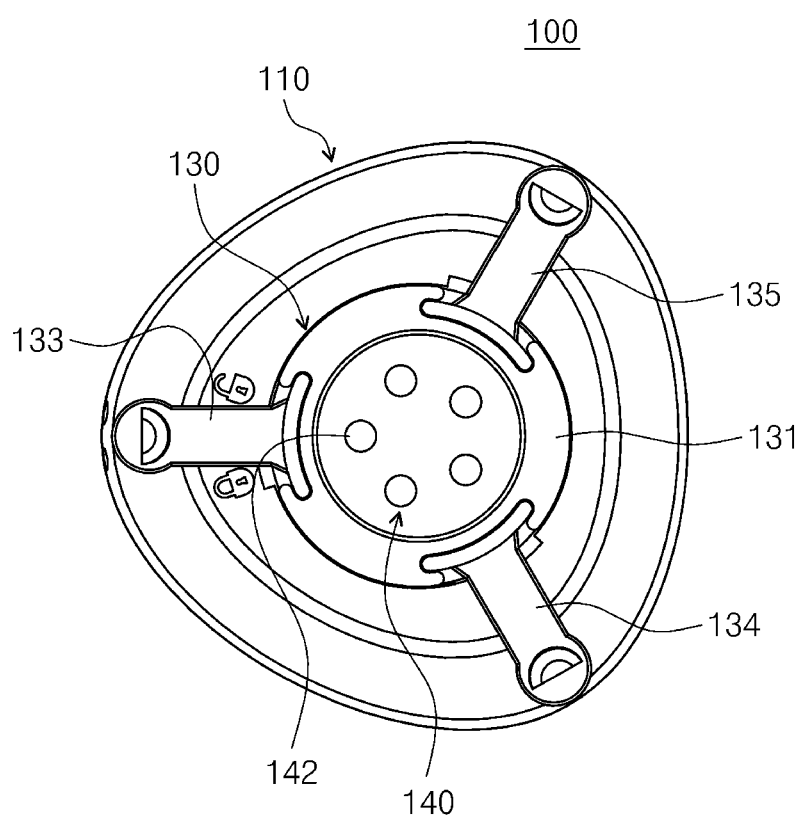
FIG. 4 is a bottom view of the iontophoresis-based patch type medicine absorption device according to the embodiment of the inventive concept.
Figure 5:
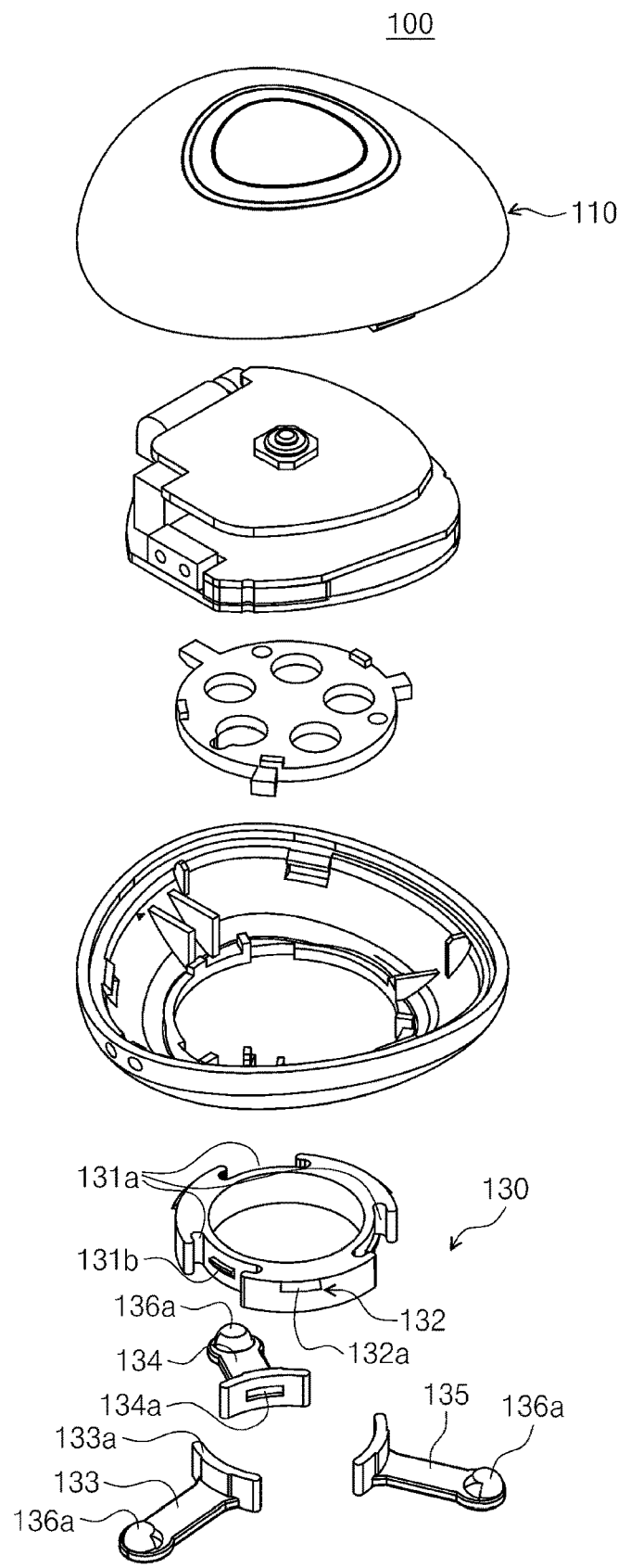
FIG. 5 is an exploded perspective view of the iontophoresis-based patch type medicine absorption device according to the embodiment of the inventive concept.
Figure 6:
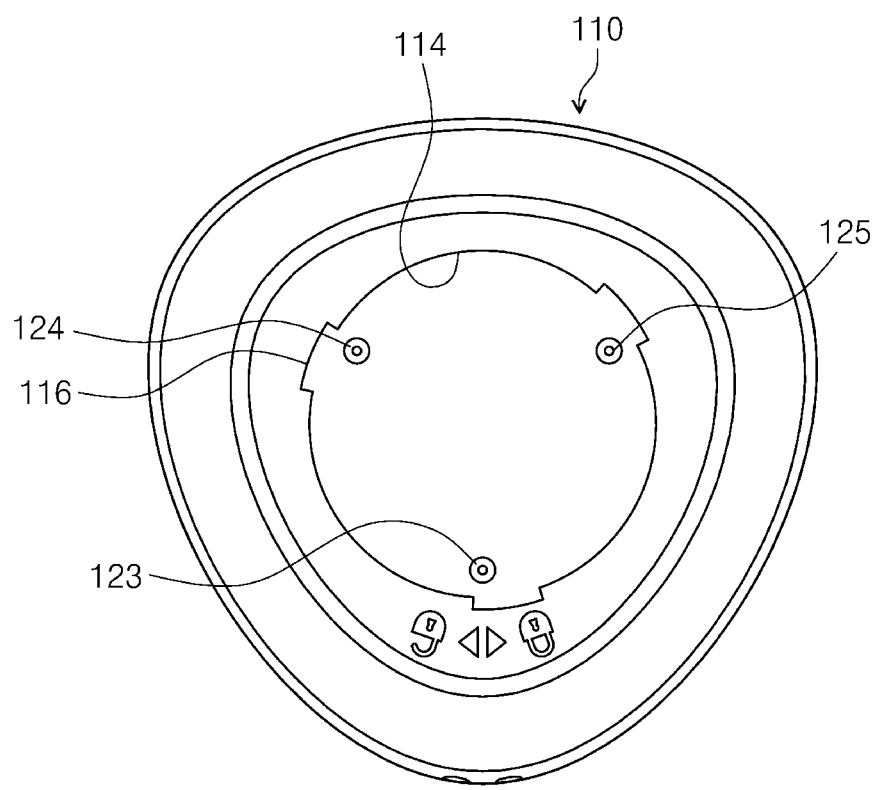
FIG. 6 is a bottom view of a body constituting the iontophoresis-based patch type medicine absorption device according to the embodiment of the inventive concept.

FIG. 1 is a view illustrating a usage state of an iontophoresis-based patch type medicine absorption device according to an embodiment of the inventive concept. FIG. 2 is a perspective view of the iontophoresis-based patch type medicine absorption device according to the embodiment of the inventive concept. FIG. 3 is a side view of the iontophoresis-based patch type medicine absorption device according to the embodiment of the inventive concept. FIG. 4 is a bottom view of the iontophoresis-based patch type medicine absorption device according to the embodiment of the inventive concept. FIG. 5 is an exploded perspective view of the iontophoresis-based patch type medicine absorption device according to the embodiment of the inventive concept. FIG. 6 is a bottom view of a body constituting the iontophoresis-based patch type medicine absorption device according to the embodiment of the inventive concept.

Referring to FIGS. 1 to 6, the iontophoresis-based patch type medicine absorption device 10 according to the embodiment of the inventive concept may include a medicine absorption device body 100 and a conductive patch 200. The medicine absorption device body 100 may be attached to the conductive patch 200 and may transfer power (voltage or micro-current) for iontophoresis to the conductive patch 200.

The medicine absorption device body 100 may allow micro-current to flow through the conductive patch 200 attached to a user's skin 20 such that a drug for skin of the conductive patch 200 is effectively absorbed through the user's skin 20 based on iontophoresis.

The drug for skin may be, for example, a drug supplied to the scalp for prevention of hair loss or facilitation of hair growth or a drug for a skin elasticity enhancement effect or a skin-lightening effect, but is not limited thereto.

In the embodiment of FIG. 1, to maximize a scalp care effect, the iontophoresis-based patch type medicine absorption device 10 including the medicine absorption device body 100 and the conductive patch 200 is attached to opposite sides of the back of the neck such that the drug is absorbed into the skin of an ascending blood region facing toward the user's scalp.

The medicine absorption device body 100 may include the body 110, a power circuit 120, a bridge 130, and a light source unit 140. The body 110 may have a small size (e.g., about 5 cm or less in size) so as to be attached to and detached from the conductive patch 200.

To efficiently generate iontophoresis on the skin through the conductive patch 200, at least part of the body 110 may be formed of a non-conductive material that does not have conductivity.

The body 110 and the bridge 130 of the medicine absorption device body 100 may have a smaller size (area) than the conductive patch 200. The medicine absorption device body 100 may have a small size of several cm (e.g., about 1 cm to about 10 cm). The medicine absorption device body 100 may be lightweight to remain stably coupled with the conductive patch 200.

The body 110 may have an interior space formed therein for accommodating the power circuit 120 that generates power, such as voltage, for iontophoresis, the light source unit 140 that outputs light to the skin, and a battery 150 that supplies operating power to the power circuit 120.

The light source unit 140 may be installed on a central portion of one surface of the body 110. A plurality of electrodes 123, 124, and 125 to which power for iontophoresis is applied from the power circuit 120 may be formed around the light source unit 140. The electrodes 123, 124, and 125 may be formed of a conductive material such as metal.

Voltage generated by the power circuit 120 may be transferred to a part of the user's body through the plurality of electrodes 123, 124, and 124, the bridge 130 coupled to the body 110, and the conductive patch 200 coupled with the bridge 130.

The bridge 130 may include a bridge body 131, a plurality of detachable parts 132, a plurality of bridge legs 133, 134, and 135, and a plurality of patch support parts 136. The bridge body 131 may have a cylindrical shape.

The bridge body 131 may be implemented with a non-conductive insulator to electrically isolate the plurality of bridge legs 133, 134, and 135. Accordingly, power of different polarities may be applied to the plurality of bridge legs 133, 134, and 135.

The plurality of detachable parts 132 may include a plurality of detachable protrusions 132a protruding along an outer circumferential surface of the bridge body 131. The body 110 may have, in the center of one surface thereof, an opening 114 for attachment and detachment of the bridge 130 and a plurality of insertion holes 116 formed along a circumferential direction from the periphery of the opening 114.

The opening 114 may have a size and shape that allows the bridge body 131 to be inserted into the opening 114. The plurality of insertion holes 116 may be concavely formed outward from the opening 114.

The plurality of insertion holes 116 may be formed in positions corresponding to the plurality of detachable protrusions 132a of the bridge 130. The bridge 130 may be coupled to the body 110 by rotating the bridge body 131 in one direction in a state in which the plurality of detachable protrusions 132a of the bridge 130 are inserted into the plurality of insertion holes 116 of the body 110.

In contrast, the bridge 130 may be separated from the body 110 by rotating the bridge body 131 in the opposite direction and detaching the plurality of detachable protrusions 132a through the plurality of insertion holes 116.

A plurality of coupling holes 131a for coupling the plurality of bridge legs 133, 134, and 135 may be formed in the bridge body 131 along the circumferential direction. The bridge 130 may include at least three bridge legs 133, 134, and 135 to remain stably coupled with the conductive patch 200.

The plurality of bridge legs 133, 134, and 135 may include a conductive material such as metal. For example, the bridge legs 133, 134, and 135 may include a conductive plastic material through which electricity passes, but is not limited thereto. Each of the bridge legs 133, 134, 135 may include an upper part 130a facing the conductive patch and a lower part 130b provided below the upper part 130a. The upper part 130a of the bridge legs 133, 134, and 135 may be formed of a conductive material, and the lower part 130b of the bridge legs 133, 134, and 135 may be formed of an insulator. Accordingly, the medicine for medical treatment and/or the functional substance for the skin care of the conductive patch may be effectively absorbed into the user's skin, since the micro-current for iontophoresis flows intensively through the conductive patch 200 brought into contact with the upper part 130a of the bridge legs 133, 134, and 135 by the insulated lower part 130b of the bridge legs 133, 134. The lower part 130b of the bridge legs 133, 134, and 135 may be formed by coating an insulation material on a lower surface of the upper part 130a of the bridge legs 133, 134, and 135. Alternatively, the lower part 130b made of an insulation material may be attached to the upper part 130a of the bridge legs 133, 134, and 135.

Coupling protrusions 133a formed at inside ends of the bridge legs 133, 134, and 135 may be coupled to the coupling holes 131a, respectively. Accordingly, the plurality of bridge legs 133, 134, and 135 may be electrically insulated from one another. The coupling protrusions 133a and the coupling holes 131a may have an arc shape.

The plurality of bridge legs 133, 134, and 135 may have a form extending in a radial direction, with the body 110 as the center. When the bridge 130 includes the three bridge legs 133, 134, and 135, the bridge legs 133, 134, and 135 may be circumferentially spaced apart from each other by an angle of 120 degrees.

The plurality of patch support parts 136 may be implemented with a plurality of stoppers 136a protruding from outside ends of the plurality of bridge legs 133, 134, and 135. The plurality of stoppers 136a may be formed to face an outward direction.

Although the bridge 130 includes the three bridge legs 133, 134, and 135 in the illustrated embodiment, the bridge 130, without being limited thereto, may include two, four or more bridge legs. When the number of bridge legs is n (n being an integer of 2 or larger), the angle between bridge legs adjacent to each other may be designed to be 360°/n to cause a uniform iontophoresis effect on the skin.

Fastening protrusions 131b for fastening the bridge legs 133, 134, and 135 may be formed on outer surfaces of the portions where the plurality of coupling holes 131a are formed in the bridge body 131. The fastening protrusions 131b may each have an inclined surface in an up/down direction.

Fastening recesses 134a may be formed on the bridge legs 133, 134, and 135. The fastening recesses 134a may be formed on radially inward surfaces of the coupling protrusions 133a inserted into the coupling holes 131a of the bridge body 131.

The fastening recesses 134a may be provided so as to be combinable with the fastening protrusions 131b of the bridge body 131. The fastening recesses 134a may each have an inclined surface having the same shape as those of the fastening protrusions 131b.

When the bridge legs 133, 134, and 135 are inserted into the coupling holes 131a of the bridge body 131, the fastening protrusions 131b of the bridge body 131 may be fastened to the fastening recesses 134a of the bridge legs 133, 134, and 135 so that the bridge legs 133, 134, and 135 may be coupled to the bridge body 131.

Figure 7:
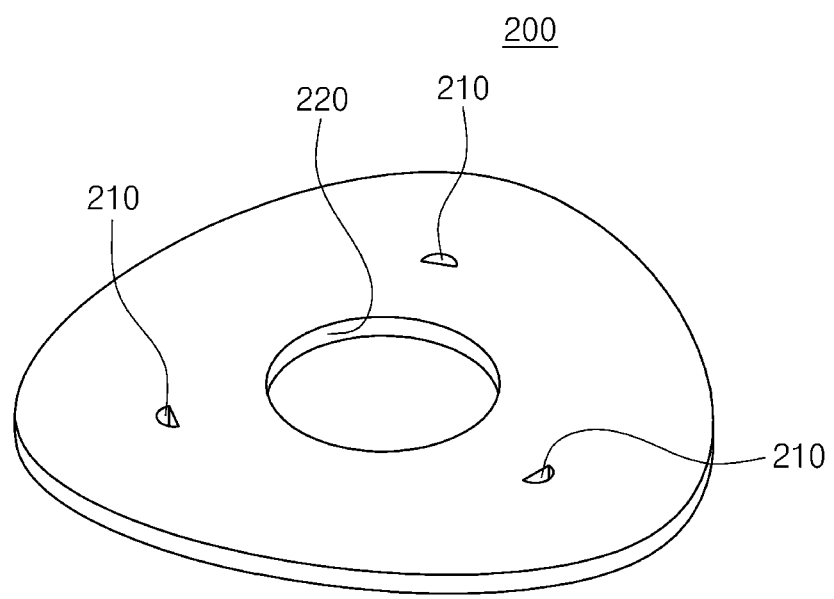
FIG. 7 is a perspective view of a conductive patch constituting the iontophoresis-based patch type medicine absorption device according to the embodiment of the inventive concept.
Figure 8:
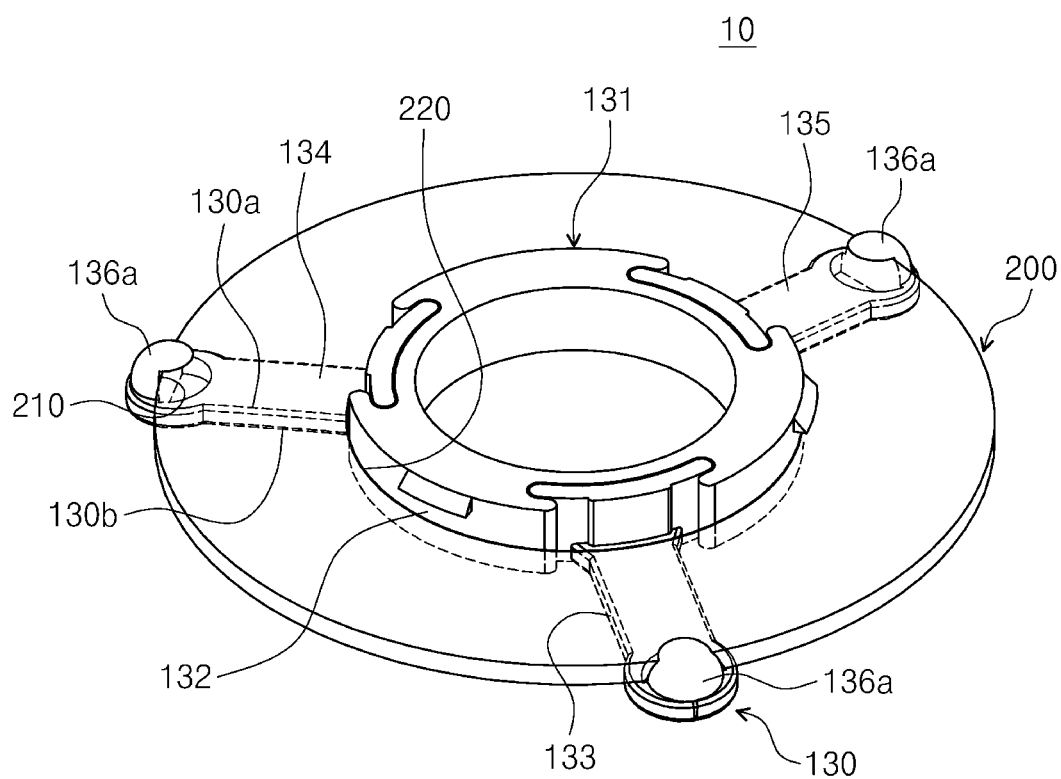
FIG. 8 is a perspective view illustrating a state in which a bridge is coupled to the conductive patch constituting the iontophoresis-based patch type medicine absorption device according to the embodiment of the inventive concept.
Figure 9:
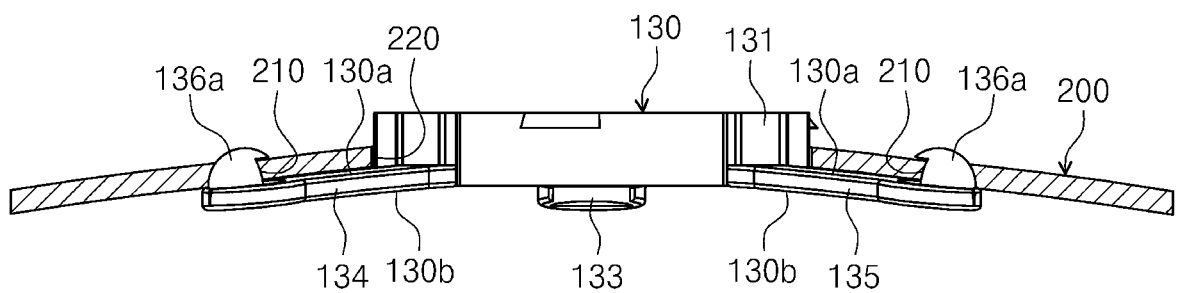
FIG. 9 is a sectional view illustrating the state in which the bridge is coupled to the conductive patch constituting the iontophoresis-based patch type medicine absorption device according to the embodiment of the inventive concept.

FIG. 7 is a perspective view of the conductive patch constituting the iontophoresis-based patch type medicine absorption device according to the embodiment of the inventive concept. FIG. 8 is a perspective view illustrating a state in which the bridge is coupled to the conductive patch constituting the iontophoresis-based patch type medicine absorption device according to the embodiment of the inventive concept. FIG. 9 is a sectional view illustrating the state in which the bridge is coupled to the conductive patch constituting the iontophoresis-based patch type medicine absorption device according to the embodiment of the inventive concept.

Referring to FIGS. 7 to 9, for a coupling of the bridge 130 and the conductive patch 200, the conductive patch 200 may include a plurality cut-away portions 210 formed in positions corresponding to the plurality of stoppers 136a. The conductive patch 200 may contain a medicine for medical treatment or a functional substance in the form of a water-soluble gel. The medicine or the functional substance may include, for example, ionic molecules having a medical effect or functionality for skin care (e.g., a substance having negative charges).

The plurality of cut-away portions 210 may be formed along a circumferential direction of the conductive patch 200. The plurality of cut-away portions 210 may have a size and shape that allows the plurality of stoppers 136a to be inserted into the plurality of cut-away portions 210.

As the plurality of stoppers 136a are inserted into the plurality of cut-away portions 210 of the conductive patch 200, the bridge 130 may be coupled to the conductive patch 200. The conductive patch 200 may have an opening 220 into which the bridge body 131 is inserted.

The plurality of stoppers 136a may be formed to face the outward direction (the radial direction) such that the medicine absorption device body 100 is stably supported on the conductive patch 200 by the bridge 130.

When the bridge 130 is coupled to the body 110 in a state in which the conductive patch 200 is coupled to the bridge 130, the conductive patch 200 is disposed between the body 110 and the plurality of bridge legs 133, 134, and 135, and the conductive patch 200, the bridge 130, and the body 110 remain stably coupled together.

The plurality of bridge legs 133, 134, and 135 may be formed of a conductive material such as metal. When the bridge 130 is coupled to the body 110, the coupling protrusions 133a of the plurality of bridge legs 133, 134, and 135 of the bridge 130 may be brought into contact with the plurality of electrodes 123, 124, and 125 of the power circuit 120.

The light source unit 140 may emit visible light and/or near infrared light. The light generated by the light source unit 140 may reach the user's skin through the opening 114 of the body 110, a central portion of the bridge body 131 of the bridge 130, and the opening 220 of the conductive patch 200.

The light source unit 140 may include one or more light sources 142. The light sources 142 may be implemented with light emitting diodes (LEDs). The light source unit 140 may provide a skin care function by stimulating tissue cells in a dermal layer of the skin using LED light that penetrates deep into the skin.

The light source unit 140 may operate in three or more light-emitting modes, including a first light-emitting mode for emitting red light, a second light-emitting mode for emitting blue light, and a third light-emitting mode for emitting red/blue light.

In the first light-emitting mode, the light source unit 140 may emit red light for preventing skin aging and soothing a sensitive scalp. The red light emitted in the first light-emitting mode may have a wavelength range of 600 nm to 700 nm.

The red light emitted in the first light-emitting mode may penetrate deep into the skin to transfer light energy and may soothe sensitive skin. In the first light-emitting mode, near infrared light may be emitted together to perform complex skin care.

In the second light-emitting mode, the light source unit 140 may emit blue light for an improvement in skin trouble or skin or hair elasticity enhancement. The blue light emitted in the second light-emitting mode may have a wavelength range of 405 nm to 415 nm. The blue light emitted in the second light-emitting mode may enhance elasticity inside the skin.

In the third light-emitting mode, the light source unit 140 may emit red and blue light for an increase in skin blood flow. The red light emitted in the third light-emitting mode may have a wavelength range of 800 nm to 900 nm. The red and blue light emitted in the third light-emitting mode may provide a complex care effect. In the third light-emitting mode, near infrared light may be emitted together to enable complex skin care.

In an embodiment, the medicine absorption device body 100 may apply voltage for iontophoresis and may simultaneously emit red light, blue light, and/or near infrared light to the skin from the light source unit 140. Accordingly, the medicine absorption device body 100 may allow the medicine for medical treatment or the functional substance of the conductive patch 200 to be more effectively absorbed into the skin.

Figure 10:
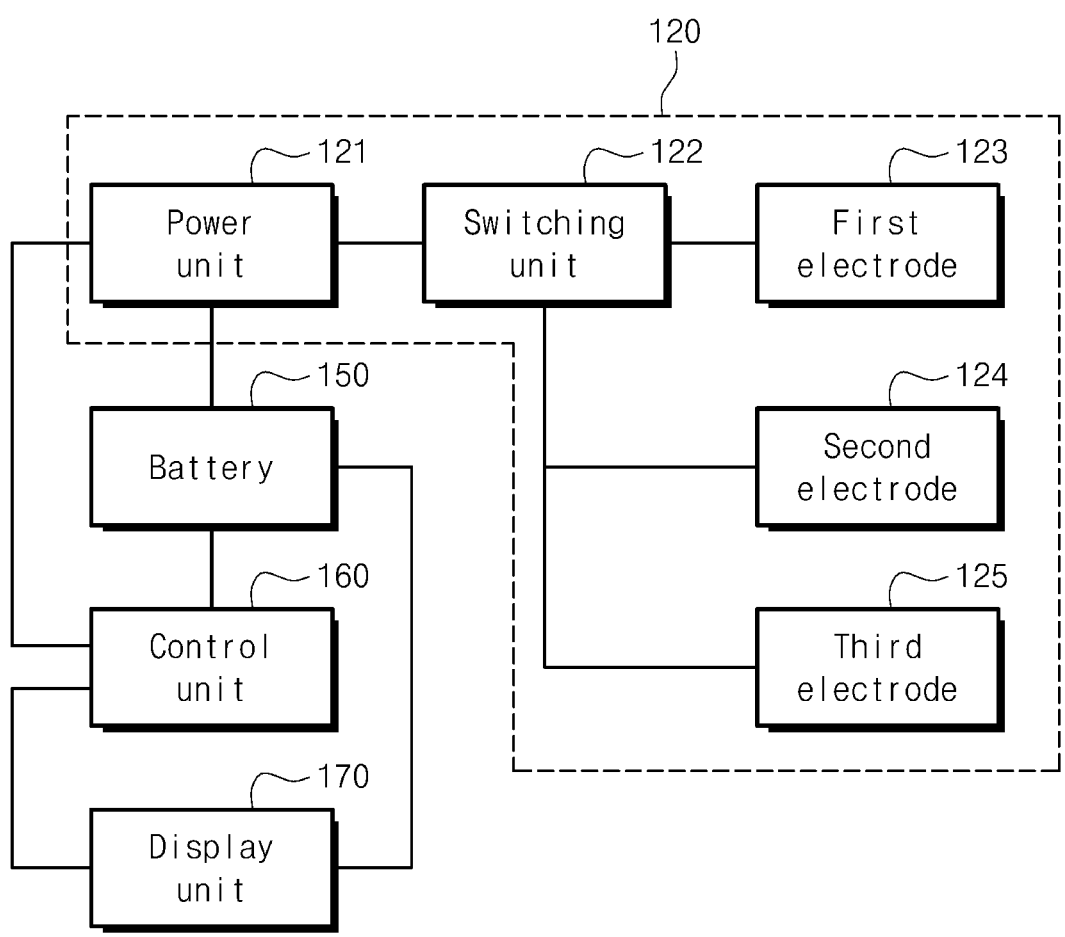
FIG. 10 is a view illustrating a configuration of a power circuit constituting the iontophoresis-based patch type medicine absorption device according to the embodiment of the inventive concept.

FIG. 10 is a view illustrating a configuration of the power circuit constituting the iontophoresis-based patch type medicine absorption device according to the embodiment of the inventive concept. Referring to FIGS. 1 to 10, a power unit 121 of the power circuit 120 may apply power of a first polarity (e.g., a positive polarity) to one or more of the plurality of electrodes 123, 124, and 125 and may apply power of a second polarity (e.g., a negative polarity) opposite to the first polarity to the remaining electrode(s).

Accordingly, when the plurality of bridge legs 133, 134, and 135 are brought into contact with the plurality of electrodes 123, 124, and 125, the power of the first polarity may be applied to one or more of the plurality of bridge legs 133, 134, and 135 by the power unit 121 of the power circuit 120, and the power of the second polarity different from the first polarity may be applied to the remaining bridge leg(s).

The power may be DC power and may be AC power or pulse power. When AC power is supplied, AC power of a first phase may be applied to some of the plurality of bridge legs 133, 134, and 135, and AC power of a second phase may be applied to the rest. In this case, the AC power of the first phase and the AC power of the second phase have opposite polarities at a specific time point.

When power is applied to the plurality of coupling protrusions 133a formed at the inside ends of the plurality of bridge legs 133, 134, and 135, the power is radially transferred through the plurality of bridge legs 133, 134, and 135 arranged in a form that radially extends. Accordingly, micro-current for iontophoresis flows through the entire surface of the conductive patch 200 brought into contact with the bridge legs 133, 134, and 135.

That is, while remaining coupled with the conductive patch 200 by the plurality of bridge legs 133, 134, and 135, the bridge 130 may radially expand micro-power for iontophoresis through the conductive patch 200 and may allowing micro-current to flow through the entire conductive patch 20.

Accordingly, the medicine for medical treatment or the functional substance of the conductive patch 200 may be more effectively absorbed into the skin by generating iontophoresis on the user's skin surface through the entire surface of the conductive patch 200.

More specifically, when voltage is applied to the user's skin surface after the conductive patch 200 is attached to a desired skin area of the user in a state in which the conductive patch 200 and the medicine absorption device body 100 are coupled together, the plurality of bridge legs 133, 134, and 135 allow micro-current to flow through the entire conductive patch 200, and a potential difference occurs in the skin.

Accordingly, the liquid medicine or functional substance in a charged state that is contained in the conductive patch 200 may be effectively absorbed into the skin by the micro-current flowing through the entire conductive patch 200.

The battery 150 may be implemented with, for example, a lithium battery. A charging part 152 may be provided on one side of the body 110. The charging part 152 may receive power from the outside and may charge the battery 150 of the medicine absorption device body 100.

As the battery 150 is able to be charged, the medicine absorption device body 100 may be wirelessly used and may be easy to carry and use.

The power circuit 120 includes the power unit 121 that generates power for causing iontophoresis on the user's skin. The power circuit 120 may be implemented with, for example, a printed circuit board (PCB). The components of the power circuit 120 may be controlled by a control unit (controller) 160 including at least one processor.

The power circuit 120 may be connected with the charging part 152 and may be configured to charge the battery 150 using the charging part 152. Furthermore, the power circuit 120 may be connected with the light source unit 140 and may control operation of the light source unit 140.

An input unit 112 may be provided on the body 110. The input unit 112 may include one or more input buttons. The input unit 112 may be configured to control ON/OFF of power (e.g., pulse power) by the power circuit 120 and transfer an ON/OFF input signal of iontophoresis.

In addition, the input unit 112 may include input buttons for transferring input signals for ON/OFF of the light source unit 140 and transition between light-emitting modes (e.g., the first to third light-emitting modes described above).

A display unit (display) 170 for displaying an operating state of the medicine absorption device body 100 may be provided on the body 110. The display unit 170 may display whether the medicine absorption device body 100 operates, by using a display method such as emitting light.

The power circuit 120 may include a switching unit 122 that sequentially switches power applied to the plurality of electrodes 123, 124, and 125. The switching unit 122 may sequentially apply power of the first polarity to the first electrode 123, the second electrode 124, and the third electrode 125.

While power of the first polarity is applied to any one of the electrodes 123, 124, and 125 by the switching unit 122, power of the second polarity opposite to the first polarity may be applied to the other electrodes. Accordingly, power of the second polarity is sequentially applied to the first electrode 123, the second electrode 124, and the third electrode 125 by the switching unit 122.

As power of different polarities is sequentially applied to the electrodes 123, 124, and 125 by the switching unit 122, the distribution of power applied to the conductive patch 200 through the bridge legs 133, 134, and 135 brought into contact with the electrodes 123, 124, and 125 is changed.

Accordingly, changing power may be applied through the conductive patch 200 to prevent concentration of micro-current on a specific skin area of the user and prevent a non-uniform iontophoresis effect for each local area of the skin to which the conductive patch 200 is attached.

Figure 11:
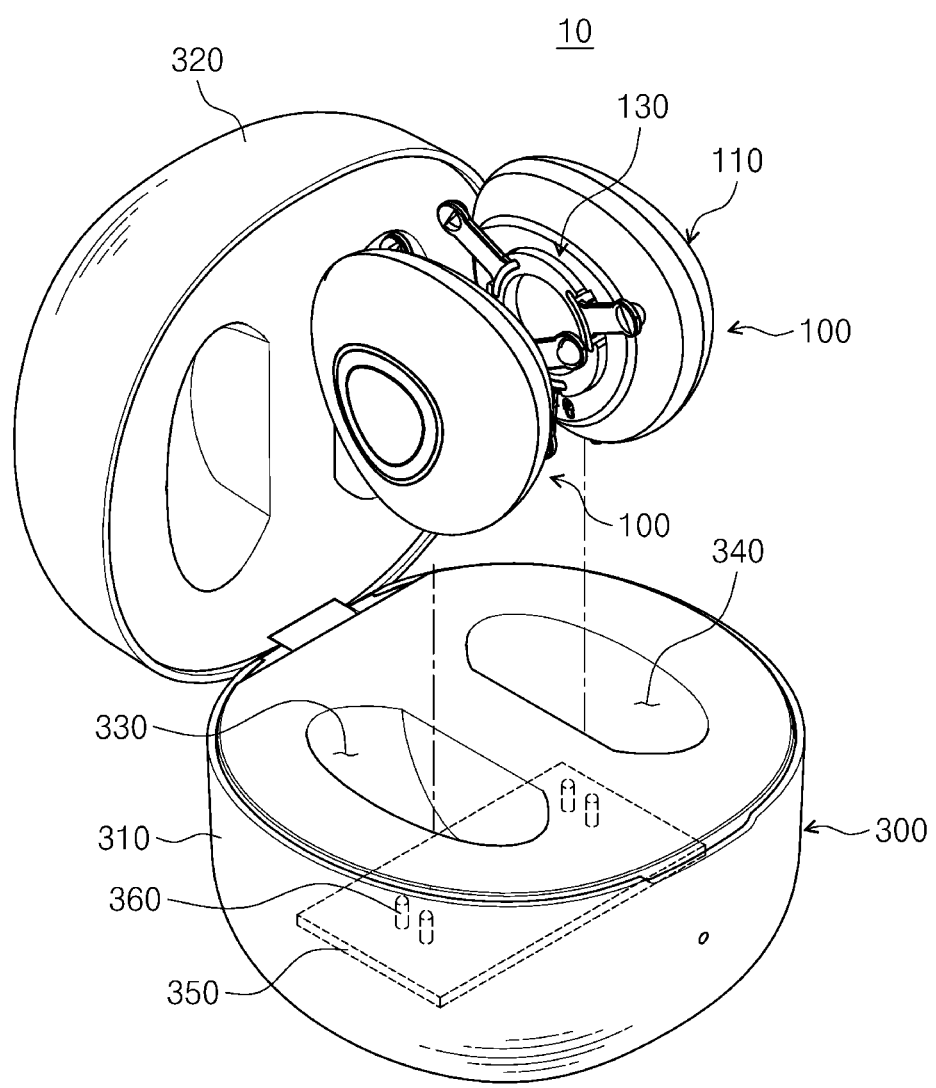
FIG. 11 is a view illustrating a charging case constituting the iontophoresis-based patch type medicine absorption device according to the embodiment of the inventive concept.

FIG. 11 is a view illustrating a charging case constituting the iontophoresis-based patch type medicine absorption device according to the embodiment of the inventive concept. Referring to FIG. 11, the iontophoresis-based patch type medicine absorption device 10 according to the embodiment of the inventive concept may further include the charging case 300 for charging the medicine absorption device bodies 100.

The charging case 300 may include a case body 310 and a cover 320 that opens and closes the case body 310. The charging case 300 may include receiving recesses 330 and 340 for receiving the medicine absorption device bodies 100 and a charger 350 for charging, through the charging parts, the medicine absorption device bodies 100 received in the receiving recesses 330 and 340. The charger 350 may charge, through charging pins 360, the batteries of the medicine absorption device bodies 100 received in the receiving recesses 330 and 340.

Hereinafter, a method for using the above-described iontophoresis-based patch type medicine absorption device 10 according to the embodiment of the inventive concept will be described. The user may couple the conductive patch 200 and the medicine absorption device body 100 by coupling the conductive patch 200 and the bridge 130 and coupling the bridge 130 to the body 110.

In a state of attaching the conductive patch 200 to a skin area, the user may operate the medicine absorption device body 100 to apply iontophoresis power. Accordingly, the medicine or the functional substance may be absorbed into the skin by iontophoresis for a predetermined period of time (e.g., several to tens of minutes) in the state in which the conductive patch 200 and the medicine absorption device body 100 are attached to the skin area.

Because the medicine absorption device body 100 is coupled to the conductive patch 200 by the plurality of bridge legs 133, 134, and 135 and is compact and light-weight, the medicine absorption device body 100 may remain stably coupled to the conductive patch 200 while being used in the state of being attached to the skin. Furthermore, because the user does not have to hold the medicine absorption device body 100 with the hands, the user may conveniently perform medicine absorption and/or skin care by iontophoresis while doing other works with the hands.

Moreover, the iontophoresis-based patch type medicine absorption device 10 according to the embodiment of the inventive concept may allow the medicine the functional substance to be absorbed into the skin, by generating a potential difference in the skin through micro-current by an iontophoresis function. Accordingly, the iontophoresis-based patch type medicine absorption device 10 may allow the medicine or the functional substance to be effectively absorbed into the skin, compared to a method of allowing a functional substance to be absorbed into a scalp only by hands or attaching a patch containing a functional substance.

Accordingly, the iontophoresis-based patch type medicine absorption device 10 according to the embodiment of the inventive concept may allow the user to easily perform skin care and may allow the medicine or functional substance to be effectively absorbed into the skin by iontophoresis. In addition, when the inventive concept is used to prevent hair loss or facilitate hair growth, the inventive concept may efficiently and effectively facilitate hair growth and may prevent hair loss.

In the above-described embodiment, the conductive patch 200 has the opening 220 into which the bridge body 131 is inserted. However, the conductive patch 200 that does not have the opening 220 may be attached to a front side of the bridge 130, and iontophoresis may be generated on the user's skin through the plurality of bridge legs 133, 134, and 135 and the conductive patch 200.

According to the embodiments of the inventive concept, the iontophoresis-based patch type medicine absorption device may allow the medicine or the functional substance for skin care to be effectively absorbed into the user's skin by causing iontophoresis on the user's skin through the conductive patch.

Furthermore, the iontophoresis-based patch type medicine absorption device may remain stably coupled to the conductive patch and may radially expand an iontophoresis generation area caused by micro-current.

Moreover, the iontophoresis-based patch type medicine absorption device may transfer power (voltage or micro-current) for iontophoresis in the state of being coupled to the conductive patch attached to the user's skin and may allow the user to conveniently perform medicine absorption or skin care.

In addition, the iontophoresis-based patch type medicine absorption device may generate uniform iontophoresis on the user's skin to which the conductive patch is attached, by controlling distribution of micro-current transferred through the conductive patch.

Figure 12:
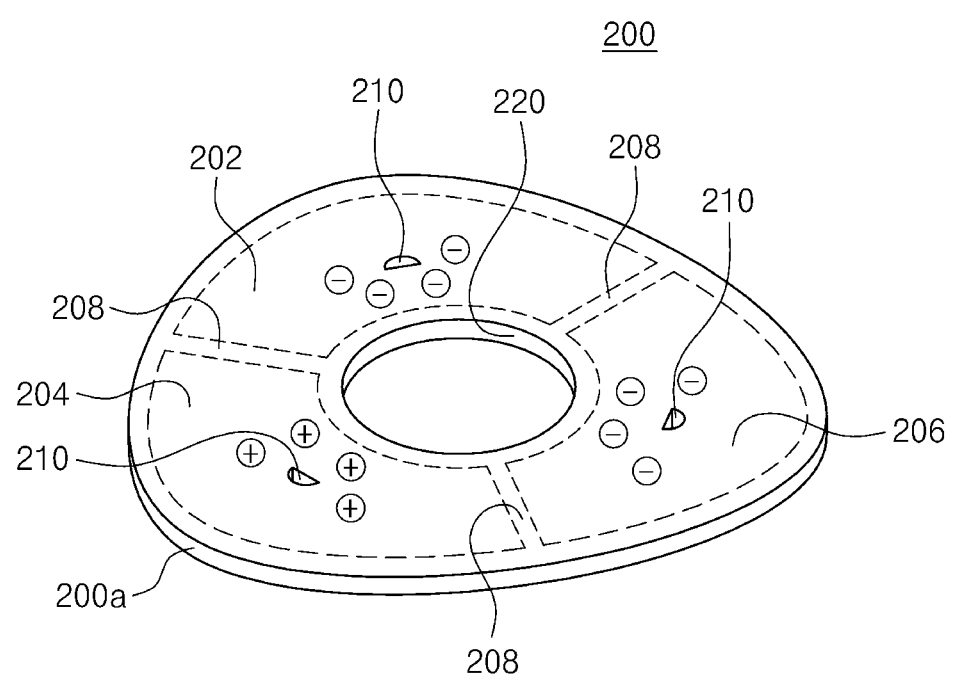
FIG. 12 is a perspective view of a conductive patch constituting the iontophoresis-based patch type medicine absorption device according to another embodiment of the inventive concept.
Figure 13:
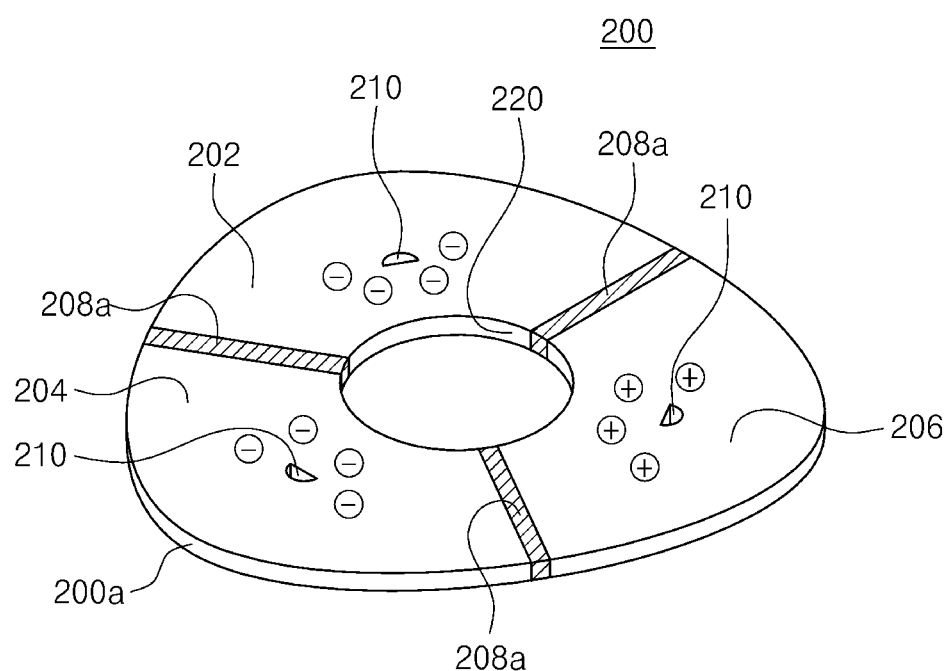
FIG. 13 is a perspective view of a conductive patch constituting the iontophoresis-based patch type medicine absorption device according to still another embodiment of the inventive concept.

FIG. 12 is a perspective view of a conductive patch constituting the iontophoresis-based patch type medicine absorption device according to another embodiment of the inventive concept. FIG. 13 is a perspective view of a conductive patch constituting the iontophoresis-based patch type medicine absorption device according to still another embodiment of the inventive concept.

The conductive patch 200 may have a multi-division patch structure in which a plurality of sub-patches 202, 204, and 206 are insulated from each other. The sub-patches 202, 204, and 206 of the conductive patch 200 may be multi-divided in accordance with the number of bridge legs 133, 134, and 135 corresponding to the number of electrodes.

The sub-patches 202, 204, and 206 of the conductive patch 200 may be independently supplied with (−) and (+) power. To this end, the sub-patches 202, 204, and 206 of the conductive patch 200 may be completely separated from each other and insulated from each other, or may be insulated by an insulator 208*a*.

In one embodiment, the sub-patches 202, 204, and 206 may be provided in one patch body 200*a*. The sub-patches 202, 204, and 206 may be formed by absorbing medical drugs or functional materials for skin care into separated areas of the patch body 200*a* made of an insulating material (see FIG. 12).

Alternatively, the sub-patches 202, 204, and 206 may be formed by absorbing medical drugs or skin care functional materials into the patch body 200*a* partitioned by one or more insulators 208*a*(see FIG. 13).

The number of sub-patches 202, 204, and 206 constituting the conductive patch 200 is not limited to three as shown, and may be variously modified according to the number of electrodes of the bridge.

Meanwhile, the conductive patch 200 may be provided with an adhesive patch having an adhesive function for attaching to the user's skin and/or a release paper detachably attached to the adhesive surface of the patch. The release paper may protect the adhesive surface of the patch by protecting the adhesive surface of the patch from contamination and foreign substances and preventing gel components of the patch from drying out. Accordingly, the release paper may maintain an adhesive strength of the patch. Moreover, the adhesive strength of the conductive patch 200 may be increased by absorbing a drug in the form of a gel that can be attached to the skin.

The plurality of sub-patches may receive the power for the iontophoresis from corresponding electrode and corresponding bridge leg respectively. According to the embodiments shown in FIGS. 12 and 13, (−) or (+) power (voltage or current) is independently applied to each of a plurality of areas of the sub-patches 202, 204, and 206 of the conductive patch 200, thus the medicine of the conductive patch 200 can be absorbed into the user's sking more effectively.

Hereinabove, although the inventive concept has been described with reference to the exemplary embodiments and the accompanying drawings, the inventive concept is not limited thereto, but may be variously modified and altered by those skilled in the art to which the inventive concept pertains. For example, suitable results may be achieved if the described techniques are performed in a different order, and/or if components in a described system, architecture, device, or circuit are combined in a different manner and/or replaced or supplemented by other components or their equivalents. Therefore, the scope of the inventive concept is defined not by the detailed description, but by the claims and their equivalents, and all variations within the scope of the claims and their equivalents are to be construed as being included in the inventive concept.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An iontophoresis-based patch type medicine absorption device for allowing a medicine for medical treatment or a functional substance for skin care to be absorbed into a user's skin by iontophoresis, the iontophoresis-based patch type medicine absorption device comprising:
   a medicine absorption device body configured to generate power to cause the iontophoresis,
   wherein the medicine absorption device body includes:
      a body having an interior space;
      a power circuit provided in the interior space, the power circuit including a power unit configured to generate the power for the iontophoresis and one or more electrodes to which the power is applied;
      a bridge provided so as to be combinable with the body and configured to receive the power through the one or more electrodes; and
      a conductive patch containing the medicine for medical treatment or the functional substance for the skin care and having conductivity, the conductive patch being provided so as to be detachable from the user's skin,
   wherein the bridge includes:
      a bridge body provided so as to be combinable with the body;
      a plurality of bridge legs arranged along a circumferential direction of the bridge body;
      a detachable part including a plurality of detachable protrusions protruding along an outer circumferential surface of the bridge body; and
      a plurality of patch support parts provided on the plurality of bridge legs to support the conductive patch,
   wherein the conductive patch is supported between the body and the plurality of bridge legs,
   wherein an upper part of each of the bridge legs is formed of a conductive material, and a lower part of each of the bridge legs is formed of an insulator, so that the medicine for medical treatment or the functional substance for the skin care of the conductive patch is effectively absorbed into the user's skin by causing the iontophoresis effectively on the user's skin through the conductive patch.

2. The iontophoresis-based patch type medicine absorption device of claim 1, wherein the plurality of bridge legs are configured to receive the power through the one or more electrodes.

3. The iontophoresis-based patch type medicine absorption device of claim 2, wherein the bridge body is implemented with an insulator to electrically isolate the plurality of bridge legs.

4. The iontophoresis-based patch type medicine absorption device of claim 1, wherein the power is transferred to the conductive patch through the plurality of bridge legs to allow micro-current to flow through the conductive patch, and a potential difference is generated in the user's skin by the micro-current, which flows through the conductive patch, to cause the iontophoresis.

5. The iontophoresis-based patch type medicine absorption device of claim 1, wherein the plurality of bridge legs are arranged to extend in a radial direction, with the bridge body as the center.

6. The iontophoresis-based patch type medicine absorption device of claim 5, wherein the patch support parts include a plurality of stoppers protruding from outside ends of the plurality of bridge legs, the stoppers being formed to face outward in the radial direction.

7. The iontophoresis-based patch type medicine absorption device of claim 6, wherein the conductive patch includes a plurality of cut-away portions formed in positions corresponding to the plurality of stoppers.

8. The iontophoresis-based patch type medicine absorption device of claim 7, wherein the bridge is coupled to the conductive patch by inserting the plurality of stoppers into the plurality of cut-away portions.

9. The iontophoresis-based patch type medicine absorption device of claim 7, wherein the body has, in the center of one surface thereof, an opening for attachment and detachment of the bridge, and
   wherein the body has a plurality of insertion holes formed in positions corresponding to the plurality of detachable protrusions, the insertion holes being formed along the circumferential direction from a periphery of the opening.

10. The iontophoresis-based patch type medicine absorption device of claim 9, wherein the bridge body is provided to be inserted into the opening, and the plurality of detachable protrusions are inserted through the plurality of insertion holes.

11. The iontophoresis-based patch type medicine absorption device of claim 9, wherein the bridge is coupled to the body by rotating the detachable protrusions inserted through the insertion holes.

12. The iontophoresis-based patch type medicine absorption device of claim 9, further comprising:
   a light source unit installed on a central portion of one surface of the body and configured to output light for skin care to the user's skin,
   wherein the conductive patch has an opening into which the bridge body is inserted, and
   wherein the light reaches the user's skin through the opening of the body, a central portion of the bridge body, and the opening of the conductive patch.

13. The iontophoresis-based patch type medicine absorption device of claim 1, wherein a plurality of coupling holes for a coupling of the plurality of bridge legs and the bridge body are formed in the bridge body along the circumferential direction, and
   wherein the plurality of bridge legs include a plurality of coupling protrusions formed at inside ends of the bridge legs and coupled to the coupling holes.

14. The iontophoresis-based patch type medicine absorption device of claim 13, wherein the coupling protrusions are brought into contact with the electrodes in a state in which the bridge is coupled to the body.

15. The iontophoresis-based patch type medicine absorption device of claim 14, wherein power of a first polarity is applied to one or more electrodes among a plurality of electrodes of the power circuit, and power of a second polarity opposite to the first polarity is applied to the remaining electrodes.

16. The iontophoresis-based patch type medicine absorption device of claim 15, wherein the power of the first polarity is applied to some of the plurality of bridge legs in a state in which the coupling protrusions are brought into contact with the electrodes, and
wherein the power of the second polarity is applied to the other bridge legs.

17. The iontophoresis-based patch type medicine absorption device of claim 1, wherein the power circuit further includes:
a switching unit configured to sequentially switch polarities of power applied to the plurality of bridge legs.

18. The iontophoresis-based patch type medicine absorption device of claim 1, wherein the medicine absorption device body further includes a charging part provided on one side of the body,
wherein the iontophoresis-based patch type medicine absorption device further comprises a charging case configured to charge the medicine absorption device body, and
wherein the charging case includes a receiving recess configured to receive the medicine absorption device body and a charger configured to charge, through the charging part, the medicine absorption device body received in the receiving recess.

19. The iontophoresis-based patch type medicine absorption device of claim 1, wherein the conductive patch includes a plurality of sub-patches provided in a patch body, the plurality of sub-patches being insulated from each other,
wherein each of the plurality of sub-patches is configured to receive the power for the iontophoresis from each of the one or more electrodes and each of the plurality of bridge legs.

20. An iontophoresis-based patch type medicine absorption device for allowing a medicine for medical treatment or a functional substance for skin care to be absorbed into a user's skin by iontophoresis, the iontophoresis-based patch type medicine absorption device comprising:
a medicine absorption device body configured to generate power to cause the iontophoresis,
wherein the medicine absorption device body includes:
a body having an interior space;
a power circuit provided in the interior space, the power circuit including a power unit configured to generate the power for the iontophoresis and one or more electrodes to which the power is applied;
a bridge provided so as to be combinable with the body and configured to receive the power through the one or more electrodes; and
a conductive patch containing the medicine for medical treatment or the functional substance for the skin care and having conductivity, the conductive patch being provided so as to be detachable from the user's skin,
wherein the bridge includes:
a bridge body provided so as to be combinable with the body; and
a plurality of bridge legs arranged along a circumferential direction of the bridge body,
wherein the conductive patch is supported between the body and the plurality of bridge legs,
wherein an upper part of each of the bridge legs is formed of a conductive material, and a lower part of each of the bridge legs is formed of an insulator, so that the medicine for medical treatment or the functional substance for the skin care of the conductive patch is effectively absorbed into the user's skin by causing the iontophoresis effectively on the user's skin through the conductive patch,
wherein a plurality of coupling holes for a coupling of the plurality of bridge legs and the bridge body are formed in the bridge body along the circumferential direction, and
wherein the plurality of bridge legs include a plurality of coupling protrusions formed at inside ends of the bridge legs and coupled to the coupling holes.

* * * * *